US008158353B2

(12) United States Patent
Bulte et al.

(10) Patent No.: US 8,158,353 B2
(45) Date of Patent: Apr. 17, 2012

(54) SPECIES-SPECIFIC AND QUANTITATIVE DETECTION OF CNS TISSUE IN MEAT AND MEAT PRODUCTS

(75) Inventors: Michael Bulte, Reinhardshain (DE); Holger Schonenbrucher, Giessen (DE); Amir Abdulmawjood, Giessen (DE)

(73) Assignee: Justus-Liebig-Universitat Giessen, Giessen (DE)

( * ) Notice: Subject to any disclaimer, the term of this patent is extended or adjusted under 35 U.S.C. 154(b) by 1195 days.

(21) Appl. No.: 10/584,270

(22) PCT Filed: Dec. 13, 2004

(86) PCT No.: PCT/DE2004/002723
§ 371 (c)(1),
(2), (4) Date: Jun. 22, 2007

(87) PCT Pub. No.: WO2005/061726
PCT Pub. Date: Jul. 7, 2005

(65) Prior Publication Data
US 2009/0233271 A1 Sep. 17, 2009

(30) Foreign Application Priority Data
Dec. 23, 2003 (DE) ................................. 103 61 489

(51) Int. Cl.
*C12Q 1/68* (2006.01)
*C12P 19/34* (2006.01)
*C07H 21/04* (2006.01)

(52) U.S. Cl. ...................... 435/6.12; 435/91.2; 536/24.3
(58) Field of Classification Search .................. None
See application file for complete search history.

(56) References Cited

FOREIGN PATENT DOCUMENTS
WO        WO 99/50661         10/1999

OTHER PUBLICATIONS

Raghavendra et al. Inhibition of microglial activation attenuates the development but not existing hypersensitivity in a rat model of neuopathy. J. Pharmacol. Experim. Therapeut. (2003) vol. 306, No. 2, pp. 624-630.*

Fahrenkrug et al. Porcine gene discovery by normalized cDNA-library sequencing and EST cluster assembly. Mammal. Genome (2002) 13:475-478.*
Lowe et al. A computer program for selection of oligonucleotide primers for polymerase chain reactions. Nucleic Acids Res. (1990) vol. 18, No. 7, pp. 1757-1761.*
Bouchard, P. B. taurus mRNA for glial fibrillary acidic protein. GenBank submission Y08255, submitted Sep. 19, 1996, pp. 1-3.*
Fahrenkrug et al. 261236 MARC 2PIG Sus scrofa cDNA 5-, mRNA sequence. GenBank submission BF443658, submitted Dec. 1, 2000, pp. 1-3.*
"Reverse Transcription-Polymerase Chain Reaction Assay for Species-Species Detection of Bovine Central Nervous System Tissue in Meat and Meat Products" by C. Seyboldt et al.; *Journal of Food Protection*; vol. 66, No. 4, 2003, pp. 644-651.
"Molecular Biological Detection of Tissues of Central Nervous System in Meat Products" by Bianca Lange et al.; *Berl. Münch. Tierärztl. Wschr*; No. 116, 2003, pp. 467-473.
"The Detection of Central Nervous System Tissue on Beef Carcasses and in Comminuted Beef" by G.R. Schmidt et al.; *Journal of Food Protection*; vol. 64, No. 12, 2001, pp. 2047-2052.
"Performance Comparison of Two Analytical Methods for the Detection of Tissues of the Central Nervous System in Sausages: Results of an Interlaboratory Study" by Marie-Elisabeth Agazzi et al.; *Eur Food Res Technol*; No. 215, 2002, pp. 334-339.
"Real Time RT-PCR Spinal Assessment of the Temporal Regulation of Glial Activation and Proinflammatory Cytokines in a Rat Model of Neuropathy" by F.Y. Tanga et al.; *Society for Neuroscience*; Online Program No. 696.19; 2003.
"Exposure to PCBS Causes Suppression of Nueral-Immune Response Genes in C6 Glioblastoma Cells" by A.M. Jelaso et al.; *Society for Neuroscience*; Online Program No. 710.12; 2003.
"Transcriptional Profiling in Human Epilepsy: Expression Array and Single Cell Real-Time qRT-PCR Analysis Reveal Distinct Cellular Gene Regulation" by Albert J. Becker et al.; *Molecular Neuroscience*; vol. 13, No. 10, Jul. 19, 2002.

* cited by examiner

*Primary Examiner* — Kenneth R. Horlick
*Assistant Examiner* — David Thomas
(74) *Attorney, Agent, or Firm* — Clark & Brody

(57) ABSTRACT

The present invention concerns a method for the species-specific and quantitative detection of CNS tissue in meat and meat products of the ruminant species bovine, ovine and caprine or porcine by a real-time PCR method, using glial fibrillary acidic protein (GFAP) messenger (m)-RNA. The method is very reliable and can be easily conducted even in heat-treated samples.

16 Claims, 4 Drawing Sheets

Figure 1:
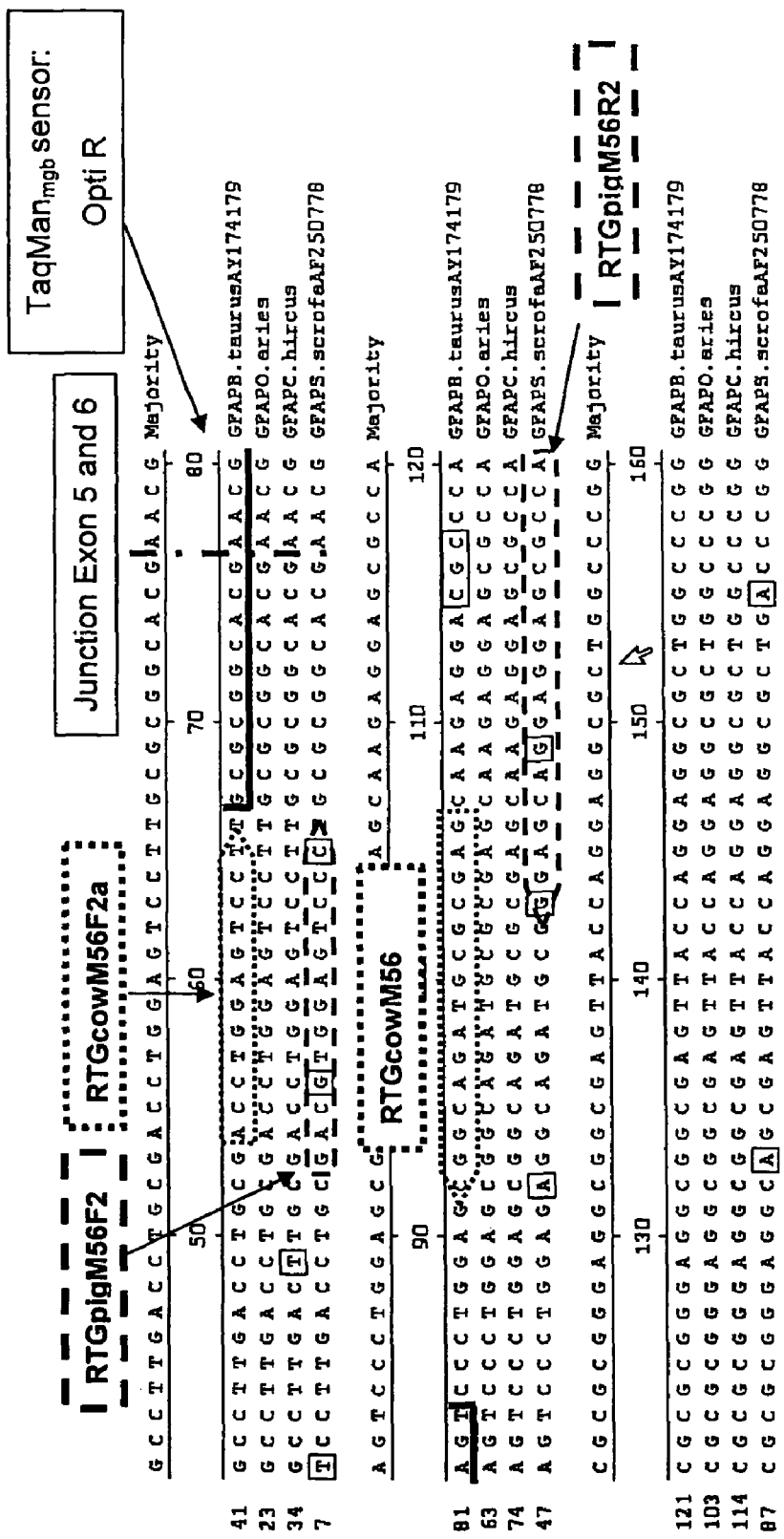

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial
<220> FEATURE:
<223> OTHER INFORMATION: GFAP-gene Exon 5 and Exon 6
<220> FEATURE:
<221> NAME/KEY: forward primer RTGcowM56F2a
<222> LOCATION: (1)..(19)
<223> OTHER INFORMATION: primer for determination BSE-riskmaterial from
      cow, sheep and goat

<400> SEQUENCE: 1
acctgcgacc tggagtcct                                                   19

<210> SEQ ID NO 2
<211> LENGTH: 15
<212> TYPE: DNA
<213> ORGANISM: Artificial
<220> FEATURE:
<223> OTHER INFORMATION: GFAP-gene Exon 5 and Exon 6
<220> FEATURE:
<221> NAME/KEY: reverse primer RTGcowM56R2a
<222> LOCATION: (1)..(15)
<223> OTHER INFORMATION: determination of BSE-riskmaterial from cow,
      goat and sheep

<400> SEQUENCE: 2
ctcgcgcatc tgccg                                                       15

<210> SEQ ID NO 3
<211> LENGTH: 17
<212> TYPE: DNA
<213> ORGANISM: Artificial
<220> FEATURE:
<223> OTHER INFORMATION: GFAP-gene Exon 5 and Exon 6
<220> FEATURE:
<221> NAME/KEY: TaqManmgb-probe OptiR
<222> LOCATION: (1)..(17)
<223> OTHER INFORMATION: Determination of BSE riskmaterial from cow,
      sheep and goat

<400> SEQUENCE: 3
actcgttcgt gccgcgc                                                     17

<210> SEQ ID NO 4
<211> LENGTH: 20
<212> TYPE: DNA
<213> ORGANISM: Artificial
<220> FEATURE:
<223> OTHER INFORMATION: GFAP-gene Exon 5 and Exon 6
<220> FEATURE:
<221> NAME/KEY: forward primer RTGpigM56F2
<222> LOCATION: (1)..(20)
<223> OTHER INFORMATION: Determination of BSE riskmaterial from pig

<400> SEQUENCE: 4
gacctgcgac gtggagtccc                                                  20

<210> SEQ ID NO 5
```

-continued

```
<211> LENGTH: 18
<212> TYPE: DNA
<213> ORGANISM: Artificial
<220> FEATURE:
<223> OTHER INFORMATION: GFAP-gene Exon 5 and Exon 6
<220> FEATURE:
<221> NAME/KEY: reverse primer RTGpigM56R2
<222> LOCATION: (1)..(18)
<223> OTHER INFORMATION: Determination of BSE riskmaterial from pig

<400> SEQUENCE: 5
tggcgctcct cctgctcc                                                 18

<210> SEQ ID NO 6
<211> LENGTH: 17
<212> TYPE: DNA
<213> ORGANISM: Artificial
<220> FEATURE:
<223> OTHER INFORMATION: GFAP-gene Exon 5 and Exon 6
<220> FEATURE:
<221> NAME/KEY: OptiR TaqManmgb probe
<222> LOCATION: (1)..(17)
<223> OTHER INFORMATION: Determination of BSE riskmaterial from pig

<400> SEQUENCE: 6
actcgttcgt gccgcgc                                                  17
```

SPECIES-SPECIFIC AND QUANTITATIVE DETECTION OF CNS TISSUE IN MEAT AND MEAT PRODUCTS

The present invention concerns a method for the species-specific and quantitative detection of CNS tissue in meat and meat products from bovine, ovine and caprine animals as well as porcine animals by means of a real-time PCR method using glial fibrillary acidic protein (GFAP) messenger (m)-RNA.

TECHNICAL STATE OF THE ART

Since the first cases of bovine spongiform encephalopathy (BSE) in dairy bovine became known in the United Kingdom in 1985, approx. 5 million bovine have already been killed due to an already existing infection or within the scope of preventive measures. Within the United Kingdom alone, the economic damage to date amounts to more than $ 6 million (SMITH, 2003).

BSE belongs to the sphere of Transmissible Spongiform Encephalopathy (TSE), which can develop in humans and a number of mammals due to misfolded proteins, so-called prions ($PrP^{sc}$). By now, there is no longer any scientific doubt that the new variant of the Creutzfeld Jakob Disease (vCJD), which occurs in humans, constitutes the human form of BSE (COLLINGE et al., 1996; DEALLER, 1998). In spite of intensive research and considerable efforts, according to the current state of knowledge, all forms of the TSE diseases are resistant to therapy and generally terminal. Besides this conclusion, drawn at the "International Prion Conference" in Munich in October 2003, one additional aggravating factor is that to date, no diagnostic systems are available which reliably enable the detection of an infection in humans or animals before the occurrence of clinically apparent diseases. As before, one has to rely on a post mortem diagnosis to verify a disease from this sphere.

The causative agent, the pathomorphological form of the prion protein ($PrP^{sc}$) is considered to be the trigger of a number of other TSE diseases occurring in animals. Among those are scrapie, which is predominant in ovine, and the Chronic Wasting Disease (CWD) which endemically occurs in North American types of Cervidae like deer as well as moose. The epidemiological connection between the individual TSE forms and the possibility of their transfer to humans, which can no longer be excluded, are the subject of a number of current studies. In this context, it should be noted that it was possible in several new test series to demonstrate the transferability of a $PrP^{sc}$ variant, which is pathogenic for minks, to the so-called human mouse model with the result that the conventional form of CJD was elicited in the animals as well (SIGURDSON und MILLER, 1998; COLLINGE, 2003). The pathogenetic development of BSE includes an oral path of infection via the tongue as well as the $PrP^{sc}$ replication in certain organs, esp. the spleen (LASMÉZAS et al., 2003). Against the backdrop of preventive food safety management, there is still a considerable, general demand for research in spite of the decreasing numbers of BSE cases in the European Community.

The most effective method to date to protect humans from the transfer of a prion-based disease emanating from animals (zoonosis) is, therefore, the elimination of the respective animal tissue rated as highly infectious, the so-called Specified Risk Material (SRM), from the production of food.

The following tissues are defined as SRM in the Regulation (EC) No. 999/2001 of the European Parliament and of the Council in its version from May 22, 2001, laying down rules for the prevention, control and eradication of certain transmissible spongiform encephalopathies, last modified by the Regulation (EC) No. 1139/2003 of the Council from Jun. 27, 2003 (ABl. L 160, pp. 22-32), valid as of Oct. 1, 2003: the skull excluding the mandible and including the brain and eyes, the vertebral column excluding the vertebrae of the tail, the transverse processes of the lumbar and thoracic vertebrae and the wings of the sacrum, but including dorsal root ganglia, and the spinal cord of bovine animals aged over 12 months, and the tonsils, the intestines from the duodenum to the rectum and the mesentery of bovine animals of all ages; the skull including the brain and eyes, the tonsils and the spinal cord of ovine and caprine animals aged over 12 months or which have a permanent incisor erupted through the gum, and the spleen and ileum of ovine and caprine animals of all ages.

The listing demonstrates that the SRM are primarily CNS tissue.

It must also be considered that meat from the head of bovine animals has been re-released for the commercial marketing as food as of Oct. 1, 2003, primarily out of economic interests. Due to the slaughter-technical preparation of the bodies of bovine, the possibility of contamination with CNS tissue exists, and hence, the danger of its import into the human food chain exists. Therefore, when licensing enterprises which produce meat of the head, the authorities responsible have made it a fundamental precondition that there are regular, enforced controls for CNS contamination.

The development and provision of methods for a quick and doubtless detection of risk tissue in the food chain of humans, but self-evidently of animals as well, is therefore imperatively required. The requirements of meat hygiene laws concerning the removal and elimination of TSE risk material prove the species-specific orientation of such detection systems. Simultaneously, a quantitative recording of SRM seems desirable in order to be able to mark off, for example, low-grade contamination, which can also be characterised as cross-contamination during transport, against the deliberate introduction, or the negligent contamination, of CNS tissue into the food. The brain possesses excellent emulsifying qualities; hence, before the ban it was used frequently in the production of certain meat products (esp. boiled sausage products); in the United Kingdom, it had been used technologically (up to 10% pro rata) especially in the production of "beef burgers".

In this context, it is significant that the processing of porcine brain is not prohibited by meat hygiene law; the same is true for the processing of separated poultry meat, which is primarily derived from mechanically separated turkey vertebral columns with a corresponding contamination via the spinal marrow. However, the regulations for meat and meat products indicate—without explicitly stating the species—that brain and spinal marrow are not processed in meat products (LS für Fleisch und Fleischerzeugnisse, last modified Oct. 2, 2001) (BAnz. No. 199 of Oct. 24, 2001, GMBI No. 38 p. 754 ff of Oct. 30, 2001).

In industrial production within the Federal Republic of Germany, this is sure to be obeyed; in registered, i.e. smaller enterprises (e.g. butchers, direct marketers) this may not be known or it may be interpreted and dealt with less stringently. In Eastern European countries, however, the processing of brain is still regionally wide-spread (EU Twinning Project, Slovakia, 2000).

To date, only species-unspecific and phenotypic methods are available for the detection of CNS tissue (LÜCKER et. al., 1997, 1998, 1999 and SCHMIDT et al., 2001). In those examinations, mainly the suitability of glial fibrillary acidic protein (GFAP) was tested as a marker for the detection of CNS tissue in food. However, Westernblot and/or ELISA methods based on this marker (SCHMIDT et al., 2001) enable neither a species-specific classification nor the reliable provision of quantitative data.

The patent applications concerning this matter, DE 198 14 088 C 1 and DE 198 04 216 C 2, include methods for detecting CNS tissue in products, esp. meat products, and test kits therefor. Both patent specifications refer to the possibility of quantitative detection. Those, however, are exclusively phenotypic methods. The substantial disadvantages of the species-unspecific quantification of CNS tissue described therein are:

The analysis by the conductors of the experiment is purely visual, i.e. the strength of signal in the examined sample must be measured against that of company-internal standards. This presupposes a high degree of familiarity with the method in question by the laboratory staff. At the same time, due to their differing tissue specificity, the utilised markers have highly varying degrees of suitability for the quantification of CNS tissue in meat and meat products. Anyone familiar with the subject knows that a GFAP Westernblot is suitable for a comparative visual quantification only under certain conditions at best. This is mainly due to the occurrence of different GFAP bar codes, with an additional varying intensity of the individual bars, which can deviate from each other considerably both within the same experimental approach and in comparison to the required reference material in different experimental approaches.

The enzymatic determination of the cholesterol concentration presented by LÜCKER and BÜLTE (1997) must be regarded as suitable under certain conditions at best, as high cholesterol concentrations, e.g. in the liver, can lead to false-positive signals.

Independent of an intended quantification, it must be taken into consideration that the combination of several marker proteins is required. Thus, for example, the utilisation of Neuron-specific Enolase (NSE) must be evaluated only as an unspecific screening reaction. The CNS tissue specificity of the result must be confirmed by means of GFAP in a second reaction, wherein however, no species-specific detection is possible.

Likewise, the existing ELISA method (SCHMIDT et al., 2001), and/or, formulated as RIDASCREEN® Risk Material, Enzyme immunoassay for the semiquantitative determination of risk material (r-biopharm), Art. No.: R6701, so far does not allow for reliable quantification. The fixing of required cut-off values must be denoted as premature. The corresponding results of our own examinations can only verify an estimate that can serve as a rough orientation.

BIBLIOGRAPHY

COLLINGE, J., SIDLE, K., MEADS, J., IRONSIDE, J. and HILL, A. (1996): Molecular analysis of prion strain variation and the aetiology of 'new variant' CJD. Nature 383: 685-690

COLLINGE, J. (2003): Prion propagation, strains and interspecies transmission. Abstr. Conf.: Prion diseases: from basic research to intervention concepts. Munich, 8 Oct. to 10 Oct. 2003

Condorelli, D. F., Nicoletti, V. G., Barresi, V., Ponticello, S. G., Caruso, A., Tendi, E. A., Giuffrida Stella, A. M. (1999): Structural features of the rat GFAP gene and identification of a novel alternative transcript. J. Neurosci. Res. 56 (3): 219-228.

DEALLER, S. (1998): Post-exposure prophylaxis after accidental prion inoculation. Lancet February 21: 351 (9102), Comment on: Lancet 1997 Nov. 22; 350 (9090): 1519-1520

EU-Twinning Projekt SR 88/AG 01 Hessen/Slowakei im Jahr 2000 (EU twinning project SR 88/AG 01 Hessia/Slowakia in the year 2000)

GUERTLER, M., ALTER, T., FROEB, A., LANGE, B., JOHNE, R., LUECKER, E. and FEHLHABER, K. (2003): Nucleotide sequence of the bovine glial fibrillary acidic protein (GFAP) gene. Direct submission to Genbank, 14 Jan. 2003

LASMÉZAS, C. I., HERZOG, C., ETCHEGARAY, N., DORMONT, D. and DESLYS, J. P. (2003): Pathogenesis of BSE in non-human primates. Abstr. Conf.: Prion diseases: from basic research to intervention concepts. Munich, 8 Oct. to 10 Oct. 2003

Leitsätze für Fleisch und Fleischerzeugnisse, zuletzt geändert am 2 Oct. 2001 (BAnz. Nr. 199 vom 24 Oct. 2001, GMBI Nr. 38 S. 754 ff vom 30 Oct. 2001)

LÜCKER, E. und BÜLTE, M. (1997): Verfahren zum Nachweis von im Hinblick auf die bovine spongiforme Enzephalopathie (BSE) unerwünschten Zutaten in Fleischerzeugnissen. 1. Enzymatische Cholesterinbestimmung als Schnellverfahren zur Erfassung von Hirngewebe. Fleischwirtschaft 77: 836-840

LÜCKER E., EIGENBRODT, E. und BÜLTE, M. (1998): Verfahren zum Nachweis von im Hinblick auf die bovine spongiforme Enzephalopathie (BSE) unerwünschten Zutaten in Fleischerzeugnissen. 2. Referenzverfahren für den Nachweis von zentralem Nervengewebe. Fleischwirtschaft 78: 896-898

LÜCKER, E., EIGENBRODT, E., WENISCH, S., FALING, M., LEISER R. and BÜLTE, M. (1999): Development of an integrated procedure for the detection of CNS tissue in meat products using cholesterol and NSE as markers. J. Food Prot. 62 (3): 268-276

Nielsen, A. L., Holm, I. E., Johansen, M., Bonven, B., Jorgensen, P., Jorgensen, A. L. (2002): A new splice variant of glial fibrillary acidic protein, GFAP epsilon, interacts with the presenilin proteins. J. Biol. Chem. 277 (33):29983-29991.

SCHMIDT, G. R., YEMM, R. S., CHILDS, K. D., O'CALLGHAN, J. P. and HOSSNER, K. L. (2001): The Detection of Central Nervous System Tissue on Beef Carcasses and in Comminuted Beef. J. Food Prot. 64 (12): 2047-2052

SIGURDSON, C. J. and MILLER, M. W. (2003): Other animal prion diseases. Br. Med. Bull. 66:199-212

SMITH, P. G. and BRADLEY, R. (2003): Bovine spongiform encephalopathy (BSE) and its epidemiology. Br. Med. Bull. 66:185-98

Regulation (EC) No 999/2001 of the European Parliament and of the Council of 22 May 2001 laying down rules for the prevention, control and eradication of certain transmissible spongiform encephalopathies, last modified by the Regulation (EC) No 1139/2003 of the Council of 27 Jun. 2003 (ABI. L 160, pp. 22-32) valid as of 1 Oct. 2003.

YU, M., ZHAO, S., LIU, B., XIONG, T., PAN, P. and LI, K. (2001): Rapid communication: isolation and regional localisation of the porcine glial fibrillary acidic protein (GFAP) gene. J. Anim. Sci. 79 (10), 2754

Task

The task of the present invention is to correct the above described disadvantages in the current technological state of the art and provide a method for the detection of CNS tissue in meat and meat products which enables a species-specific and quantitative analysis and can be carried out easily, reliably and successfully even with meat and meat products which have been treated with heat.

Solution to the Task

This task is solved, based on the present invention, by a species-specific and quantitative method for the detection of CNS tissue in meat and meat products by means of glial fibrillary acidic protein (GFAP)-messenger (m)-RNA, and a corresponding test kit for the implementation of the method in accordance with the claims.

The method based on the present invention selectively detects the existence of CNS tissue in meat and meat products from bovine, ovine and caprine animals and, alternatively, porcine animals and in the course of the same process it allows for quantitative analysis by real-time PCR recording of glial fibrillary acidic protein (GFAP)-messenger (m)-RNA. The specific detection also occurs in heat-treated meat and meat products.

The method based on the present invention consists of the following individual steps:
a) Preparation of the sample material and RNA extraction
b) Reverse transcription of the RNA into cDNA
c) Analysis of the cDNA in real-time PCR The method based on the present invention constitutes a genotypic detection method for CNS material. It allows for the detection of the smallest traces of RNA and thereby detects even minimal CNS tissue contaminations in risk material and other biological samples.

For the first time, a species-specific classification is possible, i.e. it can be determined whether the CNS tissue material stems from bovine, ovine and caprine animals or from porcine animals. In addition, an exact quantification of the detected GFAP-cDNA and GFAP-RNA concentrations, respectively, of the listed species is achieved in the same step of the procedure.

Overall, the method makes possible, in a fast and reliable manner, the quantitative detection and the species-specific differentiation of cross-contaminations during transport and/or intentional or negligent introduction of so-called risk materials into the food.

In comparison to the known phenotypic methods, which operate exclusively in a species-unspecific fashion and on a protein basis, the combination of Reverse Transcriptase (RT)-PCR and real-time technology allows—in applying the Taq-Man principle—a clearly more sensitive procedure with which up to 0.01% of CNS tissue can be detected even in heat-treated products, which can be classified as being especially problematic for analysis. The limit for detection of the real-time PCR system, which has been determined by a method known to the expert via the analysis of a decadic dilution series, is at approx. $1.0 \times 10^{-12}$ g/PCR.

The substantial advantage of real-time PCR in comparison to conventional PCR is in the sensitivity, which has been increased by a factor of 30, and in the possibility of direct quantification. Moreover, it is apparent to the expert that thanks to the demand interval and to parallel measurements, the time-consuming and labour-intensive gel electrophoretic analysis is no longer necessary.

Independent of the sample matrix and the processing and/or degree of heating in each case, reliable verification is achieved, in combination with the sample preparation, in less than 8 hours ("one day result").

Together with the optimised sample preparation methods, which, in the combination described above, are novel to this implementation, a reliable and safe method is provided, in which the implementation and simple evaluation is possible even with less well-trained laboratory staff.

The basic principle of the method based on the present invention is the selective recording of cDNA. The basic methodical requirement for a reliable implementation of the method is, therefore, the provision of a qualitatively and quantitatively high-value cDNA sample; this is implemented, based on the present invention, by a two-step principle. Furthermore, the advantages of the reverse-transcriptase system—currently the most sensitive scientific method—are used for RNA detection, and by the utilisation of random hexamers, a reliable transcription of the entire isolated RNA, including regions rich in secondary structure, is made possible. What is particularly advantageous is the small size of the gene section and/or cDNA region analysed by real-time PCR. The mRNA target region is stable for at least 2 years even in heated meat and meat products; therefore, it is reliably detectable and quantifiable.

Additional quality-assuring measures, e.g. working within a closed system (i.e. homogenisation and lysis occur within one container) and DNAse digestion, protect from potential DNA contaminations caused by sample preparation and the transcription of the RNA, and prevent possible sources of errors which can be caused by the laboratory staff.

Due to this, the new method is clearly superior to all other methods to date.

PRACTICAL EMBODIMENTS a) Preparation of the Sample Material and RNA Extraction

For sample materials, i.e. sample or control sample to be examined, e.g. brain, spinal marrow, meat and meat products with partly high concentrations of fatty acids are used. Due to the complexity of the meat and meat products to be examined (e.g. raw sausages, tinned boiled sausages or native samples of meat from the head) the step of homogenisation, which is optimised in such a way to prevent contaminations, is important.

Besides numerous standard methods known to the expert for sample preparation in chemical food analysis, such as the utilisation of the vibratory mill, the Elvehjem-Potter, the Ultra Turrax T25 (Co. Janke & Kunkel, Staufen), one preferred method is the particularly efficient and time-saving homogenisation by means of Fast Prep 120. Here, the homogenisation step consists of a combination of vertical rotation movements and horizontal up-and-down movements. This makes appliances of this kind especially suited to meet the demands made by the heterogeneous sample matrices.

As the sample material has a particularly high concentration of fatty acids, particularly when containing CNS tissue, special demands are made to the RNA extraction.

The RNA extraction is principally carried out by means of one of the known standard methods. Those are known to the expert and described in a detailed manner in standard laboratory works, such as Sambrook, Fritsch, Maniatis, 1989, Molecular Cloning, CSH Laboratory Press, Cold Spring Harbour, N.Y. etc. The main characteristic is the RNA extraction supported by guanidine thiocyanate phenol.

For use in the extraction of the entire cellular RNA, the RNeasy® Lipid Tissue Mini Kit (Qiagen, Darmstadt) is preferred. The essential advantage of this method is that it brings the lysis and extraction on phenol basis forward, which ensures the reliable RNA extraction from matrices with a particularly high concentration of fatty acids. At the same time, a reliable and easy-to-operate preparation method is available to the user which ensures, besides the column-based RNA extraction, a reliable prevention of contamination. Furthermore, additional work steps are omitted which are known to the expert and which can influence the quality of an RNA preparation in a negative way. Among them are, especially, the production of the necessary buffer substances, the handling of the DNAse, which must be classified as being especially sensitive, and the avoidance of possible phenol contaminations. The latter inhibit the subsequent Reverse Transcriptase (RT)-PCR.

Other extraction systems available on the market so far operate on a water basis and are therefore only barely suitable. Should it be possible to use these, as other conventional guanidine thiocyanate phenol extractions, alternatively, the protocols must be modified accordingly. Thus, for example, an enhancement in the RNA yield is achieved by repeated trypsinising of the fatty rings which form after the lysis of the sample material via the column or the fixation of the tissue by adding RNA-stabilising reagencies such as RNA-Later (Co. Qiagen, Hilden) before the application of the lysis buffer.

Alternatively, the higher concentration of mRNA also occurs with polyA-based kit systems (e.g. Oligoresin®-Kit, Co. Qiagen, Hilden).

For instance, the preparation of the sample material and RNA extraction occur under the following conditions:
1.0 ml of guiacol is added to 50 mg of the sample to be examined. Subsequently, the mixture is transferred into 2.0 ml Lysing Matrix D tubes (Co. Q BIOgen, Heidelberg) for the tissue and cell digestion. The Lysing Matrix D tubes are equipped with ceramic spheres with a diameter of 1.4 mm, so that they are part of the FastRNA® Pro Green isolation system (Co. Q biogen, Heidelberg). The homogenisation takes place with the assistance of the Fast Prep 120 (Co. Q Biogene, Heidelberg) at the settings "speed level 6" and "time interval 20 seconds" with a total of 4 repetitions. The short time interval prevents the sample from overheating and thereby decreasing the RNA yield. Subsequently, 200 μl of chloroform are added. The aqueous and the organic phase are separated by micro-centrifugation at +4° C. for 15 minutes at 10,000×g. After adding the first aliquot of the washing buffer RW1, an enzymatic decomposition of the DNA with DNAse takes place (Co. Qiagen, Hilden). To achieve this, 80 μl of the prepared DNAse solution are added onto the column. The utilisation of DNAse is necessary because real-time technology also records particularly low RNA concentrations, the detection of which is aggravated by existent DANN. The subsequent steps are carried out in accordance with the protocol of the manufacturer. The elution volume is 100 μl of RNAse-free water (Co. Qiagen, Hilden). The elution pathway is implemented twice.

b) Reverse Transcription of the RNA into cDNA

The transcription of the entire isolated RNA is carried out by utilisation of a Two-Step RT-PCR system with Multi-Scribe® Reverse Transcriptase and random hexamers. It is apparent to the expert that, as a first step, reverse transcription is implemented and in a subsequent step taking place in separate reaction vessels, the analysis with real-time PCR, to be explained below, occurs. The individual components utilised for the transcription are available in the form of a ready kit such as TaqMan® Reverse Transcription Reagents (Co. Applied Biosystems, Darmstadt).

In the following passages, the Mastermix and Thermocycler conditions are rendered. It is apparent to the expert that the amount of RNA used for transcription (in μl) can be selected in a variable form for each user.

The used components are organised as follows:
RNAse-free water: 38.5 μl, 10× Reverse Transcriptase (RT) buffer: 10.0 μl, 25 mM (magnesium chloride) MgCl$_2$: 22 μl, 2'-Deoxyribonucleosid-5'-triphosphat (dNTP): 20.0 μl, random hexamers: 5.0 μl, RNAse inhibitor: 2.0 μl, Multi-Scribe®-Reverse Transcriptase (50 U/μl): 2.5 μl. As a transcription control, one RNA aliquot from an older and already successfully transcripted RNA preparation is carried over in each case.

The reverse transcription is carried out, for example, in a GeneAmp 9600-Thermocycler from the company Applied Biosystems, Darmstadt, whereby the samples are incubated at 25° C. for 10 minutes and at 48° C. for 30 minutes.

In connection with the subsequent real-time PCR analysis step, this is a Two-Step RT PCR.

The comparative quality control of the RNA preparation and the transcription process takes place via a UV spectroscopy by using the application Beckman DU-600. In each case, 3 μl of the sample are diluted 100 fold in water. As a standard, one measures against the RNA Transcription Reagents (Co. Applied Biosystems, Darmstadt). To determine the quality of the cDNA preparation, the quotient is formed from absorption at 260 nm and absorption at 280 nm ($E_{260}/E_{280}$).

To the expert, the identified $E_{260}/E_{280}$ values in the range between 1.85-1.9 document the qualitative yield of the cDNA extraction and the sensitive procedure of the two-step principle.

It is apparent to the expert that without further inventive efforts, alternative methods for reverse transcription can be utilised without leaving the protective scope of the demands. A number of commercially available systems can be selected, among them Titan One Tube RT-PCR System, Titan One Tube RT-PCR Kit and C. therm. Polymerase One Step RT-PCR System (all by Co. Roche, Mannheim).

Beyond this, it is also possible to modify the kit systems, for example, by replacing the random hexamers with specific primers or oligo-(dT)-primers.

c) Analysis of the cDNA of the GFAP Gene in Real-Time PCR

In the scientific literature available to the expert, different splice variants of the GFAP gene have been described which have different tissue tropism and are therefore also differently suitable for the selective detection of CNS. Generally, it must be considered that a scientific evaluation regarding the occurrence of GFAP variations does not exist in the species relevant for the different forms of TSE diseases. To date, extensive sequence material is only available for humans and for the rodent species mouse and rat. The present invention is geared to the delta form of the GFAP gene described in rats, which consists of 9 exons and prevails, as demonstrated by our own results with the very sensitive real-time PCR method, almost exclusively in the central nervous system and the spinal marrow. Different splice variants (e.g. the epsilon splice variant) could be used as a possible alternative target region.

The precondition for establishing this method in the species-specific detection of CNS material in ovine and caprine animals is the provision of nucleotide sequences of the GFAP gene for ovine and caprine animals and a comparative alignment for ovine, caprine, porcine and bovine animals, as both of these are not yet known by the current technical state of the art.

Information based on amino acids does exist but it is species-specific and cannot be used for the implementation of the method based on the present invention. It is therefore important, first of all, to provide extensive sequence material for bovine, ovine, caprine and porcine animals and to compare it with the sequence fragments which have so far been accessible via the gene bank.

This is carried out as follows:
Production of reference DNA for bovine, ovine, caprine and porcine animals
sequencing of the GFAP genes of bovine, ovine, caprine and porcine animals
Analysis of the GFAP sequences by means of gene structure determination and alignment As the starting material for the production of reference DNA for bovine, ovine, caprine and porcine animals, genomic DNA is extracted from striated muscles. The DNA extraction occurs by means of known DNA extraction methods, e.g. by using the Dneasy® Tissue Kit (Co. Qiagen, Hilden). The method is conducted according to the manufacturer's instructions.

The availability of an intact DNA preparation is controlled via PCR testing by means of universal primers, e.g. for the cytochrome B gene. The reference DNA is stored at −20° C.

For the sequencing of the GFAP genes of the ruminant species bovine, ovine, caprine, and the species porcine, suitable sequencing primers are utilised according to methods known to the expert and the sequencing is carried out, for example, by using the MegaBACE 1000 DNA Sequencing System (Co. Amersham Pharmacia Biotech) according to the manufacturer's instructions.

The processing of raw data is carried out via Chromas (School of Biomolecular and Biomedical Science and Technology, Griffith University, Brisbane, Queensland, Australia) and subsequent data conversion is carried out by means of the software package DNA-Star (Co. Lasergene®). For the determination of the exon-intron boundaries, different internet databases (e.g. BLAST of the NCBI genetic database) are consulted in addition to cDNA analysis and the mentioned computer programmes.

The comparison of the sequences in the GFAP sequence analysis is illustrated schematically in FIG. 1, which shows the alignment of the GFAP sub-units of bovine (*Bos taurus*), ovine (*Ovis aries*), caprine (*Caprae hircus*) and porcine (*Sus scrofa*) animals and the localisation of the utilised primers and the TaqMan$_{mgb}$ sensor. The section shown displays the areas of the adjacent exons 5 and 6 which have been selected for the primer and sensor design. Generally, there is a clearly recognisable high sequence homology within the ruminant group of bovine, ovine and caprine animals in contrast to porcine animals.

FIG. 1 shows a) the primer and sensor combination for the detection of bovine, ovine and caprine animals:
Junction between exons 5 and 6

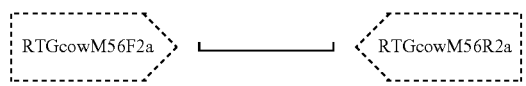

b) the primer and sensor combination for the detection of porcine animals:

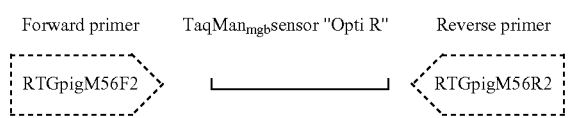

The GFAP gene sequence of bovine animals (*Bos taurus*, Guertler et al., 2003) can be viewed in the NCBI genetic database under the gene database access number AY 174179, that of porcine animals (*Sus scrofa*, Yu et al., 2001) under AF 250778.

It is apparent from the comparison of the sequences that the selected oligonucleotides have been positioned in the examined sequence section, following norms for the selection of PCR primers known to the expert, in the optimal manner to guarantee a selective recording of the GFAP gene sequences of bovine, ovine and caprine animals ⟨⎯⎯⟩.

Analogously, a further primer pair was selected in such a way that the GFAP gene sequence of porcine animals ⟨⎯⎯⟩ is amplified in a selective way.

The design of the TaqMan$_{mgb}$ sensor ⟨⎯⎯⟩ spanning the exon-exon boundary corresponds to the specification, i.e. that the junction is positioned exactly in the middle of the sensor and that temperature and G/C ratio have been aligned to the developed primers in an optimal manner. The positioning of the sensor ensures the selective amplification of cDNA. The amplification sizes (approx. 80 base pairs for bovine, ovine and caprine animals, and approx. 60 base pairs for porcine animals) are optimal according to the requirements of the real-time technology, for which scientific and technological statutes demand a product size of 50 to 150 base pairs. The low product size is an essential precondition for the guarantee of high sensitivity and specificity; furthermore, this includes a positive verification even after 2-year storage of heat-treated samples.

Thanks to the volume of the data material, and if the above-mentioned species are included, it is possible, for the first time, to present the species-specificity of the GFAP gene. Preferably, the gene segment exon 5 and exon 6 of the GFAP gene is used in order to generate species-specific primers. Likewise, a TaqMan$_{mgb}$ sensor spanning the boundary between exon 5 and exon 6 is developed.

In providing the GFAP nucleotide sequences for ovine and caprine animals, the necessary preconditions are provided for the selective species-specific recording of the cDNA of the ruminant species bovine, ovine, and caprine on one hand and the species porcine on the other.

Alternatively, other exons, e.g. exon 1, 2, 3, 4 and 7, 8 and 9 can also be used to implement the method based on the present invention, as can the regions of the different splice variants, e.g. exon 7a of the epsilon splice variant of the GFAP gene; the production of the corresponding primers is known to the expert and is easily possible without further inventive efforts. Likewise, the method based on the present invention is applied to the detection of CNS material of ruminant species generally as well as wild ruminants, as those are characterised by a similar nucleotide sequence of the GFAP gene. If the nucleotide sequence of the GFAP gene is known for other vertebrates, for example, equines such as horses or donkeys, poultry such as Galliformes like chickens and turkeys, or Anseriformes like ducks, or other mammals such as minks (Rodentia), canines or felines, the production of the corresponding primers and the implementation of the method based on the present invention are apparent to the expert.

In a preferred practical embodiment, the method is implemented in such a way that it results in the specific detection of CNS material for the ruminant species bovine, ovine and caprine and the species porcine.

Based on the nucleotide sequences of the GFAP gene for the ruminant species bovine, ovine and caprine, primer sequences and TaqMan$_{mgb}$ sensor sequences are developed, preferably by using exon 5 and exon 6.

Thereby, the method based on the present invention is carried out in such a way that the specific detection of CNS material occurs for bovine, ovine and caprine animals.

The sequences of the primers based on the present invention for the analysis of the cDNA in real-time PCR and those of the TaqMan$_{mgb}$ sensors are composed of the following nucleic acid sequences:

| Nomenclature of the | | Nucleotide sequence | Number of bases |
|---|---|---|---|
| Forward primers | RTGcowM56F2a | 5'-ACC TGC GAC CTG GAG TCC T-3' | 19 |
| Reverse primers | RTGcowM56R2a | 5'-CTC GCG CAT CTG CCG-3' | 15 |
| TaqMan$_{mgb}$ sensor | OptiR | 6-FAM-ACT CGT TCG TGC CGC GC-MGB | 17 |

Based on the nucleotide sequences of the GFAP gene of porcine animals, primer sequences and TaqMan$_{mgb}$ sensor sequences are developed, preferably by using exon 5 and exon 6.

Thereby, the method based on the present invention is conducted in such a way that the specific detection of CNS material in porcine animals is carried out.

The sequences of the primers based on the present invention for the analysis of the cDNA in real-time PCR and those of the TaqMan$_{mgb}$ sensors are composed of the following nucleic acid sequences:

| Nomenclature of the | | Nucleotide sequence | Number of bases |
|---|---|---|---|
| Forward primers | RTGpigM56F2 | 5'-GAC CTG CGA CGT GGA GTC CC-3' | 20 |
| Reverse primers | RTGpigM56R2 | 5'-TGG CGC TCC TCC TGC TCC -3' | 18 |
| TaqMan$_{mgb}$ sensor | OptiR | 6-FAM-ACT CGT TCG TGC CGC GC-MGB | 17 |

Explanations about the Nomenclature for the Primer and Sensor Combinations:

TaqMan® is a registered trademark of the company Hoffman-La Roche.

The notation mgb/MGB stands for minor groove binder and denotes a method of sensor design known to the expert with which a higher binding affinity to the target region and the selection of sensors with a shorter base sequence are made possible. Proceeding by this method has proved especially advantageous for the represented region.

FAM denotes a substance known to the expert and selected for the fluorescent dye marker of sensors which is also known as fluorescein. The use of further flurophores is in accordance with the technological standard and known to the expert.

The TaqMan$_{mgb}$ sensor based on the present invention is applied alternatively to each of the two primer pairs in each case. The real-time PCR assay which is available by means of this primer and sensor combination is, therefore, especially suitable for the species-specific and quantitative recording of CNS tissue in bovine, ovine and caprine animals as well as porcine animals. The ABI 7000 Sequence Detection System (Co. Applied Biosystems, Darmstadt) is used as an appliance for analysis.

It is suggested to alternatively supply the primers based on the present invention with a marker (fluorescence, radioactivity etc.) and to carry out the analysis by autoradiography or chemiluminescence.

The primers based on the present invention are nucleic acid molecules which bind to the GFAP gene or hybridise with it, as the case may be. Besides the listed nucleotide sequences, this comprises their fragments, derivates and allelic variants. Derivate, in this context, means that the sequences of these primers differ in one or more positions and that there is a high degree of homology. Homology, here, refers to a sequence identity of at least 40%, particularly an identity of at least 60%, preferably more than 80%, and especially preferably more than 90%. The deviations to the nucleic acid molecules described above may originate from deletion, substitution and/or insertion.

For the step of relative quantification known to the expert, cDNA from the sample material containing CNS tissue, which is previously prepared according to the process described, is employed as a decadic dilution series in each real-time PCR.

During this, the concentration of the extracted cDNA is determined via a UV spectroscopy. Subsequently, the decadic dilution series is defined as a standard within the scope of the configuration of the utilised real-time cycler and the spectroscopically determined values are entered manually into the user software of the thermocycler as a basis for calculation. The cDNA concentration of the samples to be examined is determined in relation to the standards carried over during the same PCR course.

Alternatively, it is possible to further increase the diagnostic sensitivity by using an absolute quantification by means of the so-called Housekeeping gene.

The following Mastermix conditions (50 μl stock solution) are preferred for use:

| Components for the Mastermix | Reaction mixture 1x in μl each 50 μl |
|---|---|
| TaqMan Universal PCR Master Mix (2x) | 25.0 |
| MgCl$_2$ | 0 |
| Primer 1 | 1.5 |
| Primer 2 | 1.5 |
| TaqMan sensor | 2.5 |
| Aqua dest. | 14.5 |

-continued

| Components for the Mastermix | Reaction mixture 1x in µl each 50 µl |
|---|---|
| Template DNA | 5.0 |
| Total volume | 50 µl |

The utilised reagencies are contained in the TaqMan® Universal Mastermix (Co. Applied Biosystems, Darmstadt) as a complete formulation.

The thermocycler conditions are selected as follows: Initial UNG incubation at 50° C. for 2 minutes, and activation of the AmpliTaq Gold(r) DNA polymerase (Co. Applied Biosystems, Darmstadt) occurs at 95° C. As an analysis period, 40 cycles were decided upon which comprised a denaturisation at 95° C. for 15 sec. and an annealing phase at 60° C. for 1 minute. Generally, every measurement is carried out in a duplicate mixture. The data evaluation, which consists of fixing of the threshold cycle (Ct-value) and the determination of the quantitative GFAP concentration [unit: ng/µl] in the examined sample is carried out according to the methods known to the expert.

Figure 2:
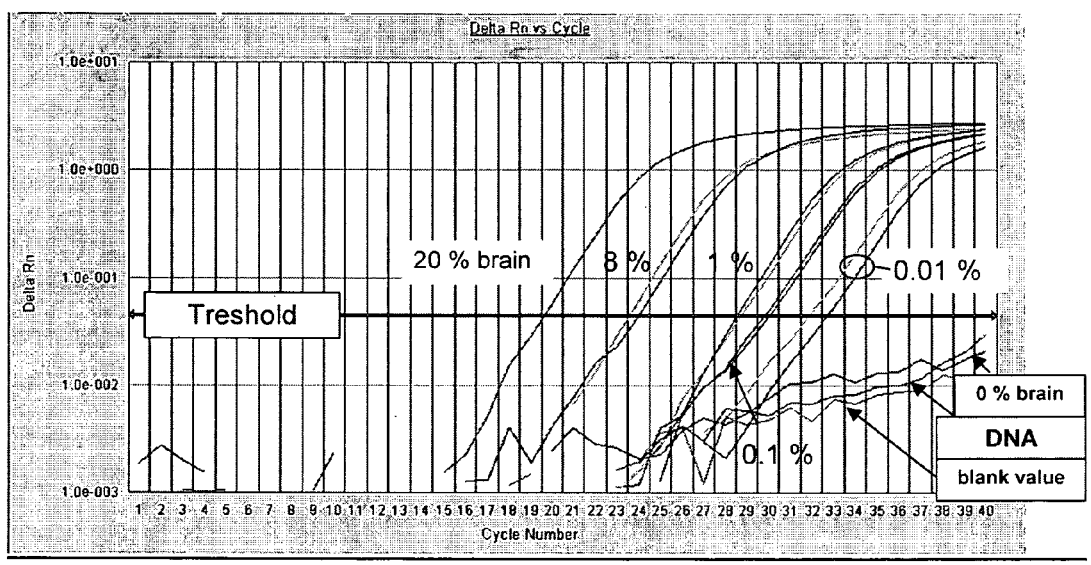

The subsequent evaluation of the results takes place, according to the procedure known to the expert which is illustrated exemplarily in FIG. 2, for the examination of raw and heat-treated meat products. FIG. 2 shows the representation of the detection boundary of the real-time PCR system.

Figure 3:
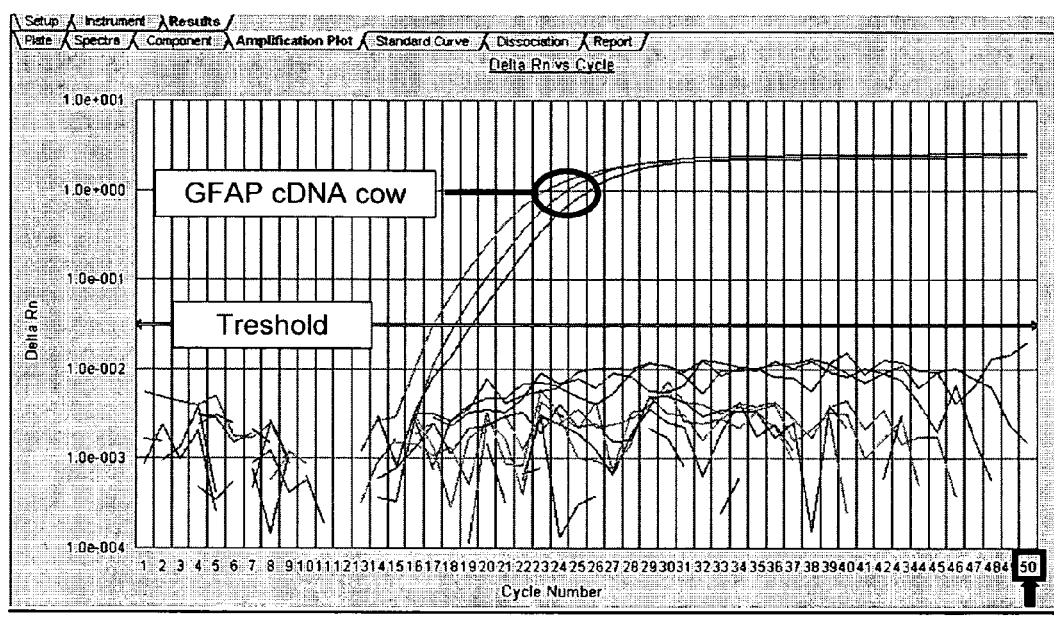
Figure 4:
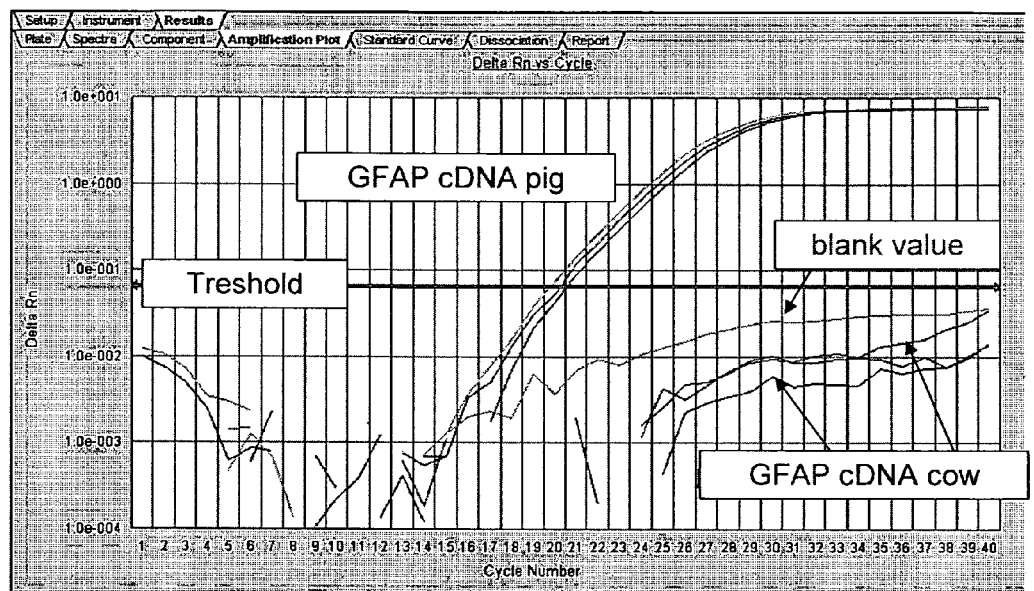

FIGS. 3 and 4 show the species-specific verification by the developed real-time PCR system. FIG. 3 shows the selective recording of GFAP cDNA of bovine animals; the non-detected species are porcine, Galliformes such as turkey and chicken, and Anseriformes such as duck. The depicted fluorescence signal detection correspondingly applies to ovine and caprine animals. FIG. 4 shows the selective recording of GFAP cDNA for porcine animals. The examiner receives the percentage of CNS concentration of the analysed meat product relevant for food law. This concentration is determined as follows:

1. The expert is familiar with the representation of the signal detection as the "Amplification plot". The fluorescence signal detection—determined by means of the threshold cycle (Ct-value)—, which is equivalent to the formation of the desired amplification, begins earlier the higher the initial GFAP concentration in the examined sample is.

As was depicted exemplarily, a threshold cycle of the Ct value of 32.4 or 33.1, respectively, corresponds to a CNS concentration of 0.01% of brain tissue in heat-treated meat products, e.g. perishable, semi-perishable, and long shelf-life foods; the same applies for raw meat products. It is known to the expert that especially long shelf-life foods, which undergo a heating process at 121° C. during their production, constitute products for which a high degree of damage to the mRNA to be detected can be expected. The extremely reliable detection rate of the developed method, even for this product group, must be regarded as a clear advantage in comparison to the previously existing methods. The examined samples are each analysed in a duplicate mixture. Therein, it is apparent to the expert that in the low-concentrated mRNA area (here: 0.01%) within one PCR mixture, fluctuations in the Ct value of 0.2 to 1.0, must be assessed as characteristic of the procedure.

With the help of the "amplification plot" it is clearly recognisable that no "false positive" reactions occur within the 0 value, i.e. the sample in which no brain is added. The selective cDNA recording is apparent by means of the DNA preparation which has been carried over. In that sample, no reaction takes place. Thus, the reliability of the real-time PCR system is ensured particularly by considering the diagnostic quality assurance.

With the method cascade based on the present invention it is possible for the first time to detect even the slightest fluctuations and/or diminutions of the GFAP concentration as they may develop, e.g. due to the extreme heat treatment of the food during the tinning process.

2. In addition, the data is issued in the form of the tabular overview known to the expert showing the study results of the analysis, which are summarised as an "Analysis Report" in the exemplarily used Real-Time Cycler Abi PRISM(r) 7000 Sequence Detection System and which bear analogous notations depending on the type of appliance that was used. Besides the Ct values, the quantitative relations in comparison to the dilution series which has been carried over are listed by nanogramme per PCR reaction [ng/PCR reaction], which allow for the following interpretation: The content of GFAP cDNA in ng/PCR mixture in the examined sample corresponds to that of a reference sample with a fixed percentage of brain additive. It is apparent to the expert that alternatively, by carrying out an absolute quantification, the GFAP concentration can be stated as the number of gene copies detected in the sample.

It must be emphasised that the electronic data recording and documentation are in accordance with the guidelines of diagnostic quality assurance for modern laboratory practice.

An embodiment of the invention relates to an easy-to-handle kit for the species-specific and quantitative detection of CNS tissue in meat and meat products containing, at least, I. Materials for the Species-Specific and Quantitative Analysis of the GFAP cDNA.

Materials for the detection of the GFAP cDNA of bovine, ovine and caprine animals for real-time PCR TaqMan consisting of: Universal PCR Master, $MgCl_2$, Primer RTGcowM56F2a 5'-ACC TGC GAC CTG GAG TCC T-3', Primer RTGcowM56R2a 5'-CTC GCG CAT CTG CCG-3' and TaqMan$_{mgb}$ sensor OptiR 6-FAM-ACT CGT TCG TGC CGC GC-MGB.

Material for the detection of the GFAP cDNA of porcine animals for real-time PCR TaqMan consists of: Universal PCR Master, $MgCl_2$, Primer RTGpigM56F2 5'-GAC CTG CGA CGT GGA GTC CC-3', Primer RTGpigM56R2 5'-TGG CGC TCC TCC TGC TCC-3' and TaqMan$_{mgb}$ sensor OptiR 6-FAM-ACT CGT TCG TGC CGC GC-MGB.

Alternatively, the test kit additionally contains:

II. Material for the RNA Extraction as Well as Suitable Reaction Buffers and/or

III. Material for the Reverse Transcription of the Extracted GFAP mRNA

For example, RNAse-free water, Reverse Transcriptase (RT) buffers, $MgCl_2$, 2'-Deoxyribonucleoside-5'-triphosphate (dNTP), Random Hexamers, RNAse Inhibitor, Reverse Transcriptase. Alternatively, the test kit contains a transcription control in the form of a GFAP mRNA for the supervision of a successful transcription process of the isolated GFAP mRNA in cDNA.

Preferably, the test kit contains an internal amplification control; it serves to supervise the correct process of the PCR analysis and eliminate "false negative" results.

Preferentially, the test kit contains reference samples for the quantification of the examined test samples. It is known to the expert that on the one hand, this is the model for the dilution series described above, as well as the addition of different samples with a defined CNS concentration. Alternatively, the reference sample is a reference gene for absolute quantification.

The test kit includes the formulation as an individual detection system just as the layout design as a Multiplex PCR.

Thanks to the teachings concerning the present invention and thanks to general scientific expertise in this technological field, manufacturers of the kit based on the present invention are familiar with how to produce, formulate and store the individual components of the kit, e.g. the buffers.

The invention claimed is:

1. A method for the species-specific and quantitative detection of central nervous system (CNS) tissue in meat and meat products, comprising the steps:
   a) preparing of the sample material and RNA extraction
   b) reverse transcribing of the RNA into cDNA
   c) analyzing of the cDNA of the glial fibrillary acidic protein (GFAP) gene in real-time PCR, wherein the real-time PCR is carried out with a pair of primers selected from the group consisting of
   a first pair of primers, namely
   SEQ ID NO 1: primer RTGcowM56F2a 5'-ACC TGC GAC CTG GAG TCC T-3' and
   SEQ ID NO. 2: primer RTGcowM56R2a 5'-CTC GCG CAT CTG CCG-3',
   a second pair of primers, namely
   SEQ ID NO. 4: primer RTGpigM56F2 5'-GAC CTG CGA CGT GGA GTC CC-3'
   SEQ ID NO. 5: primer RTGpigM56R2 5'-TGG CGC TCC TCC TGC TCC-3',
   and pairs of primers comprising a forward and a reverse primer having a sequence identity of at least 40% to said first or said second pair of primers;
   and wherein the real-time PCR is carried out using a TaqMan$_{mgb}$ sensor spanning the boundary between exon 5 and exon 6 of the GFAP gene.

2. The method according to claim 1 wherein the preparation of the sample material occurs by homogenization.

3. The method according to claim 1 wherein the RNA extraction occurs by means of lysis and extraction on phenol basis so that RNA is also extracted from matrices with a high concentration of fatty acids.

4. The method according to claim 1 wherein the real-time PCR is carried out for bovine, ovine and caprine animals with SEQ ID NO. 3 TaqMan$_{mgb}$ sensor OptiR 6-FAM-ACT CGT TCG TGC CGC GC-MGB.

5. The method according to claim 4 wherein primer RTGcowM56F2a or primer RTGcowM56R2a is used with the TaqMan$_{mgb}$ sensor OptiR.

6. The method according to claim 1 wherein the real-time PCR is carried out for porcine animals with the following primer:
   SEQ ID No. 6 TaqMan$_{mgb}$ sensor OptiR 6-FAM-ACT CGT TCG TGC CGC GC-MGB.

7. The method according to claim 6 wherein primer RTG RTGpigM56F2 or primer RTG pigM56R2 is used with the TaqMan$_{mgb}$ sensor OptiR.

8. The method according to claim 1 wherein the method is carried out in heat-treated meat and meat products.

9. A test kit for the species-specific and quantitative detection of central nervous system (CNS) tissue in meat and meat products, containing, at least, material for the species-specific and quantitative analysis of the GFAP cDNA, wherein the material for real time-PCR of the extracted GFAP mRNA for the detection of bovine, ovine and caprine animals are Universal PCR Master, MgCl$_2$, SEQ ID No. 1: primer RTGcowM56F2a 5'-ACC TGC GAC CTG GAG TCC T-3', SEQ ID No. 2: primer RTGcowM56R2a 5'-CTC GCG CAT CTG CCG-3' and SEQ ID No. 3: TaqMan$_{mgb}$ sensor OptiR 6-FAM-ACT CGT TCG TGC CGC GC-MGB and/or the material for real time-PCR of the extracted GFAP mRNA for the detection of porcine animals are Universal PCR Master, MgCl$_2$, SEQ ID No. 4: primer RTGpigM56F2 5'-GAC CTG CGA CGT GGA GTC CC-3', SEQ ID No. 5: primer RTGpigM56R2 5'-TGG CGC TCC TCC TGC TCC-3' and SEQ ID No. 6: TaqMan$_{mgb}$ sensor OptiR 6-FAM-ACT CGT TCG TGC CGC GC-MGB.

10. The test kit for the species-specific and quantitative detection of CNS tissue in meat and meat products according to claim 9, containing material for RNA extraction as well as suitable reaction buffers and/or material for the reverse transcription of the extracted GFAP mRNA.

11. The test kit for the species-specific and quantitative detection of CNS tissue in meat and meat products according to claim 9, wherein the material for the reverse transcription and the extraction of mRNA are RNAse-free water, reverse transcriptase (RT) buffers, MgCl$_2$, 2'-deoxyribonucleoside-5'-triphosphates (dNTP), random hexamers, RNAse inhibitor and reverse transcriptase.

12. The test kit for the species-specific and quantitative detection of CNS tissue in meat and meat products according to claim 9, wherein a transcription control is contained in the form of a GFAP mRNA for the supervision of a successful transcription process of the isolated GFAP mRNA into cDNA.

13. The test kit for the species-specific and quantitative detection of CNS tissue in meat and meat products according to claim 9, wherein the test kit contains a positive control in the form of the GFAP cDNA of bovine and/or porcine animals and a negative control in the form of the GFAP cDNA of bovine and/or porcine animals, an internal amplification control as well as reference samples for the quantification of the examined test samples.

14. The test kit for the species-specific and quantitative detection of CNS tissue in meat and meat products according to claim 9, wherein the reference samples are dilution series, samples with defined CNS content and/or a reference gene.

15. The method according to claim 1, wherein the sequence identity is one of at least 60%, more than 80%, and more than 90%.

16. The method according to claim 2, wherein the homogenization further comprises a combination of vertical rotation movements and horizontal up-and-down movements.

* * * * *